US010888350B2

(12) United States Patent
Nakano et al.

(10) Patent No.: US 10,888,350 B2
(45) Date of Patent: Jan. 12, 2021

(54) DEVICE HANDLE FOR A MEDICAL DEVICE

(71) Applicant: TERUMO KABUSHIKI KAISHA, Tokyo (JP)

(72) Inventors: Taiga Nakano, Sunnyvale, CA (US); Junichi Kobayashi, Cupertino, CA (US); Tomonori Hatta, Cupertino, CA (US); Kosuke Nishio, Machida (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 96 days.

(21) Appl. No.: 15/992,636

(22) Filed: May 30, 2018

(65) Prior Publication Data

US 2018/0368880 A1 Dec. 27, 2018

Related U.S. Application Data

(60) Provisional application No. 62/513,173, filed on May 31, 2017.

(51) Int. Cl.
| | |
|---|---|
| *A61B 17/32* | (2006.01) |
| *A61B 17/3207* | (2006.01) |
| *A61B 17/22* | (2006.01) |
| *A61B 1/00* | (2006.01) |
| *A61B 17/00* | (2006.01) |
| *A61B 90/00* | (2016.01) |

(52) U.S. Cl.
CPC .. *A61B 17/320758* (2013.01); *A61B 1/00066* (2013.01); *A61B 17/22012* (2013.01); *A61B 1/00027* (2013.01); *A61B 2017/00371* (2013.01); *A61B 2017/22049* (2013.01); *A61B 2017/320004* (2013.01); *A61B 2017/320733* (2013.01); *A61B 2017/320766* (2013.01); *A61B 2090/0811* (2016.02); *A61B 2217/005* (2013.01); *A61B 2217/007* (2013.01)

(58) Field of Classification Search
CPC .... A61B 17/320725; A61B 17/320783; A61B 17/32002; A61B 17/22031; A61B 17/320758; A61B 17/22012; A61B 1/00066
See application file for complete search history.

(56) References Cited

U.S. PATENT DOCUMENTS

| | | | | |
|---|---|---|---|---|
| 4,559,928 A | * | 12/1985 | Takayama | A61B 1/0052 388/838 |
| 5,026,384 A | * | 6/1991 | Farr | A61B 17/320758 606/159 |
| 5,681,336 A | * | 10/1997 | Clement | A61B 17/320758 604/96.01 |

(Continued)

*Primary Examiner* — Wade Miles
*Assistant Examiner* — Mohammed S Adam
(74) *Attorney, Agent, or Firm* — Buchanan Ingersoll & Rooney PC

(57) ABSTRACT

A device handle is disclosed for grinding substances inside a body lumen, the device handle comprising: a high-speed drive source configured to rotate a treatment member connected to a distal end of a drive shaft; and a low-speed drive source connected to a revolution shaft, and wherein the revolution shaft is configured to cause the treatment member to move about a central axis of the revolution shaft, and wherein the central axis of a proximal portion of the revolution shaft is different from a central axis of the treatment member.

18 Claims, 11 Drawing Sheets

(56) References Cited

U.S. PATENT DOCUMENTS

| | | | | |
|---|---|---|---|---|
| 5,836,868 | A * | 11/1998 | Ressemann | A61B 17/320725 606/159 |
| 6,451,036 | B1 * | 9/2002 | Heitzmann | A61B 17/320758 606/159 |
| 8,579,926 | B2 * | 11/2013 | Pintor | A61B 17/320758 606/159 |
| 8,795,306 | B2 | 8/2014 | Smith et al. | |
| 9,554,823 | B2 | 1/2017 | Weber et al. | |
| 2004/0111081 | A1 * | 6/2004 | Whitman | A61B 10/0233 606/1 |
| 2004/0243162 | A1 * | 12/2004 | Wulfman | A61M 39/06 606/167 |
| 2005/0209610 | A1 * | 9/2005 | Carrison | A61B 17/1671 606/114 |
| 2007/0085496 | A1 * | 4/2007 | Philipp | B01F 15/00409 318/139 |
| 2008/0097499 | A1 * | 4/2008 | Nash | A61B 17/320758 606/159 |
| 2010/0121361 | A1 | 5/2010 | Plowe et al. | |
| 2011/0190806 | A1 | 8/2011 | Wittens | |
| 2012/0226101 | A1 * | 9/2012 | Tinkham | A61B 1/00066 600/106 |
| 2013/0158353 | A1 * | 6/2013 | Nakamura | A61B 1/00156 600/114 |
| 2013/0172679 | A1 * | 7/2013 | Ashida | A61B 1/00156 600/114 |
| 2013/0172919 | A1 | 7/2013 | Carrison | |
| 2016/0120570 | A1 * | 5/2016 | Kobayashi | A61B 90/39 606/166 |
| 2016/0128607 | A1 * | 5/2016 | Ohno | A61B 1/00158 600/409 |
| 2016/0183967 | A1 * | 6/2016 | McGuckin, Jr. | A61B 17/320758 606/159 |
| 2017/0027611 | A1 * | 2/2017 | Adams | A61B 17/320016 |
| 2017/0209024 | A1 * | 7/2017 | Weitzner | A61B 1/0052 |
| 2017/0273698 | A1 * | 9/2017 | McGuckin, Jr. | A61B 17/00234 |
| 2018/0042641 | A1 | 2/2018 | Govari et al. | |
| 2018/0117290 | A1 * | 5/2018 | Matlock | A61B 17/24 |
| 2018/0146978 | A1 * | 5/2018 | Patel | A61B 17/320758 |
| 2018/0318133 | A1 * | 11/2018 | Clauson | A61F 9/00754 |
| 2018/0326144 | A1 * | 11/2018 | Truckai | A61M 3/0254 |
| 2018/0344349 | A1 | 12/2018 | Nakano et al. | |
| 2019/0029695 | A1 | 1/2019 | Huwais | |
| 2019/0167077 | A1 * | 6/2019 | Hancock | A61B 1/00133 |
| 2019/0193122 | A1 * | 6/2019 | Liu | G02B 23/2423 |

* cited by examiner

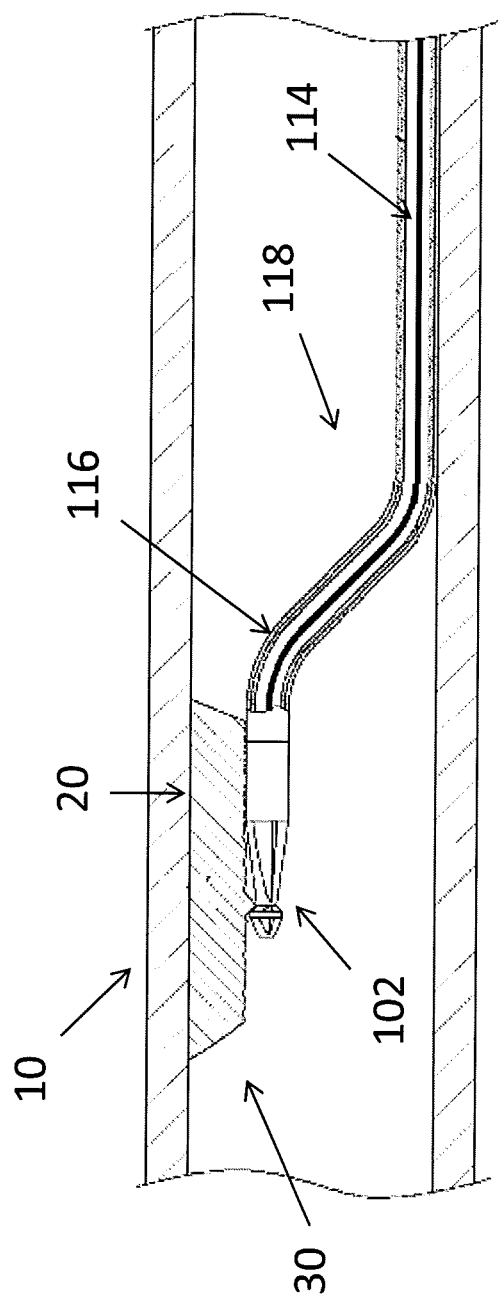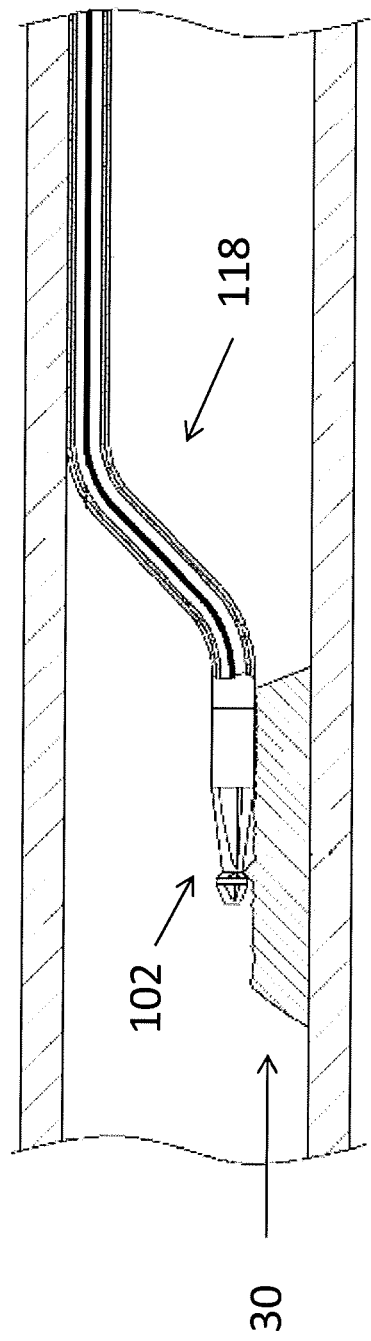

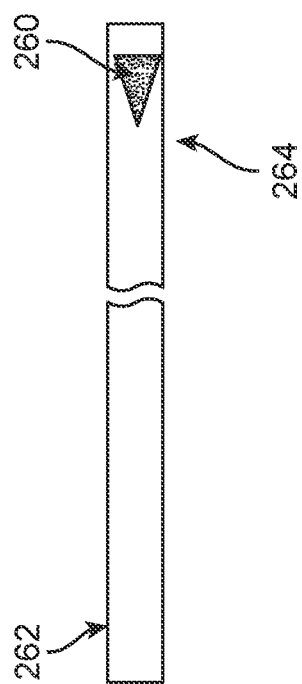
FIG. 8
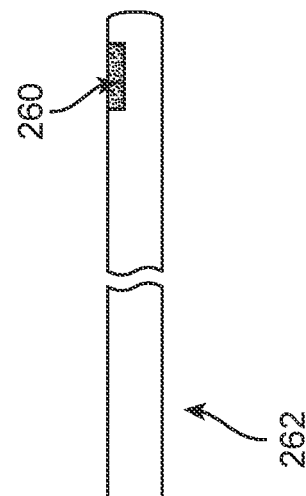
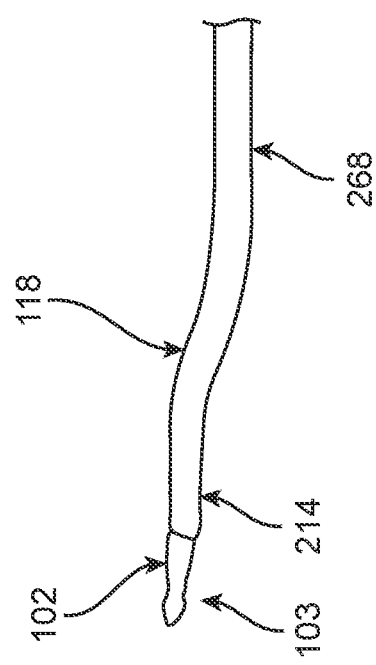
FIG. 9

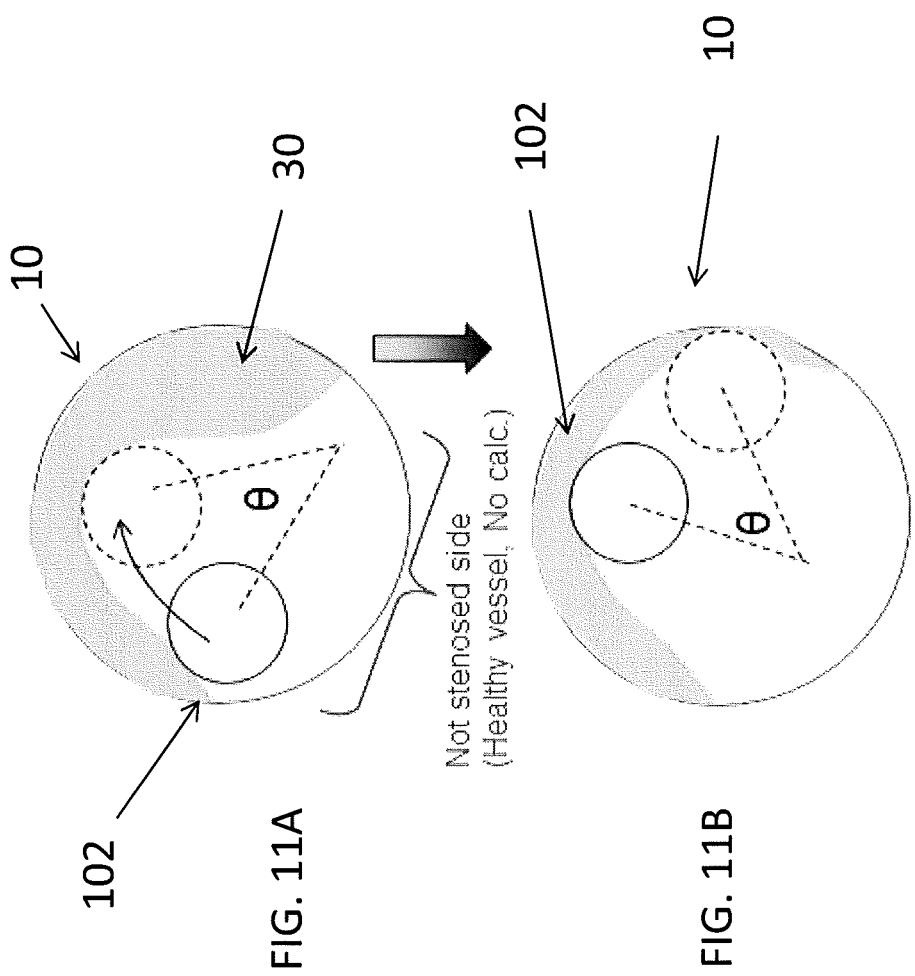

DEVICE HANDLE FOR A MEDICAL DEVICE

CROSS-REFERENCE TO RELATED APPLICATIONS

This application claims priority to U.S. Patent Application No. 62/513,173 filed on May 31, 2017, the entire content of which is incorporated herein by reference.

TECHNICAL FIELD

The present disclosure generally relates to a device handle for a medical device and method for grinding a substance from an inner wall surface of a body lumen.

BACKGROUND DISCUSSION

Medical devices are used to remove substances from a living body. As an example, an atherectomy device is used to remove arteriosclerosis from a blood vessel. The atherectomy device is typically configured to be positioned in the living body adjacent the substance to be cut and then the treatment part of the device is then rotated to cut the substance. The debris resulting from this cutting procedure is then removed from the living body. The removal of the cut-away debris can be accomplished by way of a gateway lumen passing through the atherectomy device.

Experience has shown that these known devices and methods can result in distal embolization. That is, some of the debris can create an obstruction or blockage resulting in slow flow or no flow in the peripheral vessel. When this occurs, physicians must aspirate the peripheral vessel to remove the debris forming the distal embolization. In very severe cases, it may be necessary to perform amputation.

Proposals have been made to address concerns about distal embolization. For example, some atherectomy devices are provided with an aspiration function for removing the debris by way of an aspiration port. However, these solutions have not been found to be particularly satisfactory. In some instances, choking of the aspiration port occurs, thus inhibiting or preventing a continuous aspiration of the desired region.

The atherectomy procedure for cutting substance from a living body lumen (removing arteriosclerosis from a blood vessel) typically involves the use of two different guidewires. A first coated guidewire is used to deliver the atherectomy device to the stenotic region or treatment area. After the atherectomy device is located at the desired position, the coated guidewire is removed and a second different guidewire is inserted into the atherectomy device. One way in which the second guidewire differs from the first is that the second guidewire is not coated. This second non-coated guidewire is used during operation of the atherectomy device when the treatment part is rotated at a high speed.

The reason two different guidewires are used is that the coated first guidewire is a preferred guidewire for guiding and delivering the atherectomy device to the treatment area. However, the coating on this first guidewire tends to become abraded or damaged during rotation of the treatment part. The abrasion of the rotating treatment part against the coated guidewire can produce coating fragments that may cause distal embolization.

SUMMARY

A device handle is disclosed for grinding substances inside a body lumen, the device handle comprising: a high-speed drive source configured to rotate a treatment member connected to a distal end of a drive shaft; and a low-speed drive source connected to a revolution shaft, and wherein the revolution shaft is configured to cause the treatment member to move about a central axis of the revolution shaft, and wherein the central axis of a proximal portion of the revolution shaft is different from a central axis of the treatment member.

A device handle is disclosed for grinding substances inside a body lumen, the device handle comprising: a high-speed drive source configured to rotate a treatment member connected to a distal end of a drive shaft; a low-speed drive source connected to a revolution shaft; a first activation switch for activating the low-speed drive source; wherein the first activation switch is a button in which the revolution shaft only rotates when pressure is applied to the button; a second activation switch for activating the high-speed drive source; and wherein the second activation switch is a button in which the drive shaft rotates once the button is pressed until pressed again.

A method is disclosed for grinding substances inside a living body, the method comprising: introducing a treatment member into the living body and positioning the treatment member adjacent substance in the living body to be ground; rotating the treatment member in at least a clockwise direction or a counterclockwise direction about an axis of rotation of the treatment member while the treatment member is positioned adjacent the substance to be ground in the living body to grind the substance; rotating a revolution shaft in at least a clockwise direction or a counterclockwise direction about an axis of rotation of the revolution shaft; and shearing debris resulting from the grinding of the substance to reduce a size of the debris.

BRIEF DESCRIPTION OF THE DRAWINGS

FIGS. 2A and 2B are cross-sectional views of the distal portion of the medical device, including the treatment member having a bending section positioned in a blood vessel to grind-away a substance in the blood vessel.

FIG. 8 is a view of an indicator on a revolution shaft indicating a direction of bend in accordance with an exemplary embodiment.

FIG. 9 is an illustration of bending section of the medical device and the indicator on the revolution shaft indication the direction of bend in accordance with an exemplary embodiment.

FIGS. 11A and 11B are cross-sectional views of the wiper-like action of a treatment member inside a blood vessel in accordance with an exemplary embodiment.

DETAILED DESCRIPTION

Figure 1:
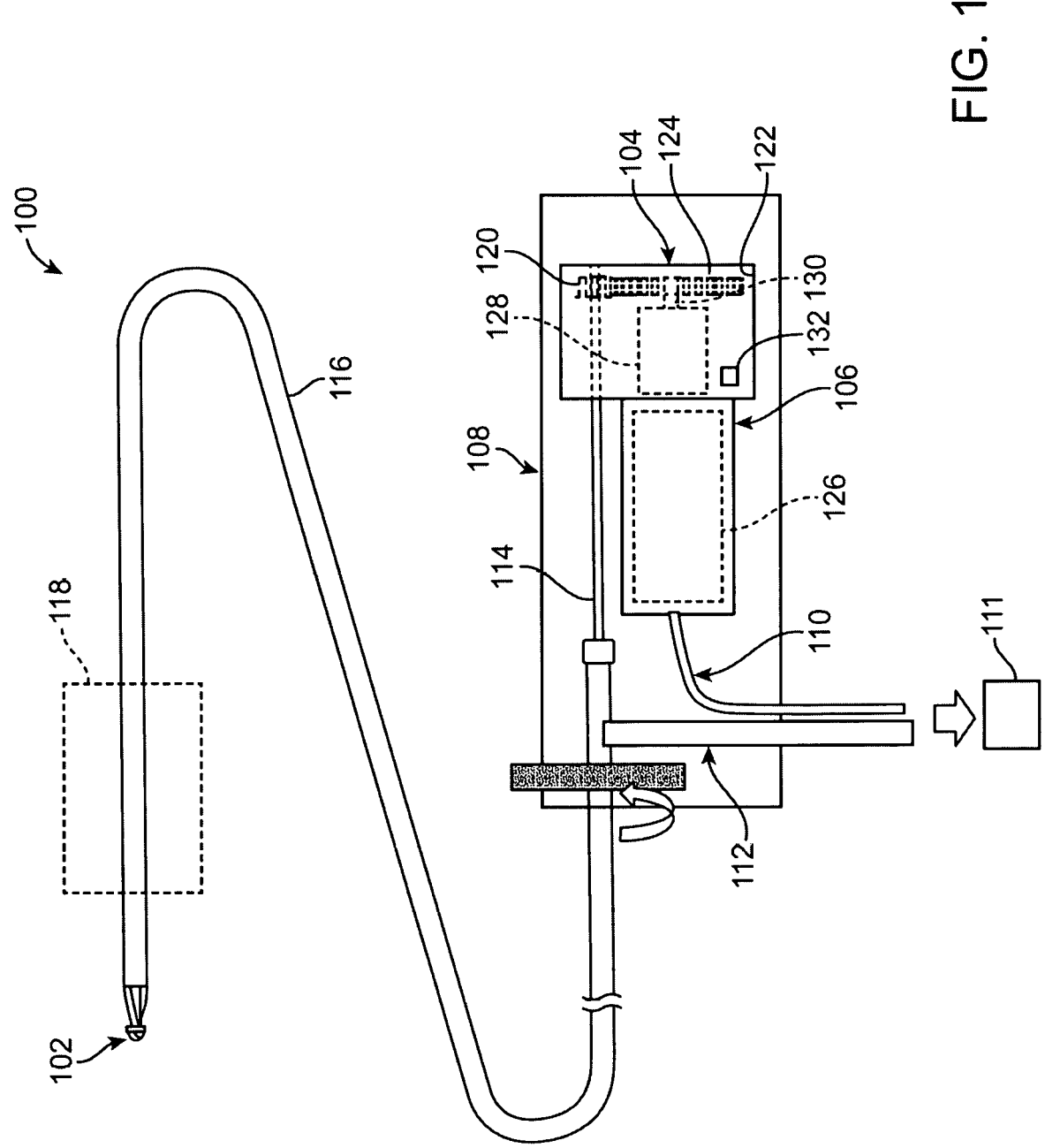
FIG. 1 is a schematic view of the medical device according to one embodiment.

Hereinafter, embodiments of the present disclosure will be described with reference to the drawings. In order to facilitate description, dimensional ratios in the drawings are exaggerated, and thus are different from actual ratios in some cases.

Hereinafter, embodiments of the present disclosure will be described with reference to the drawings. In order to facilitate description, dimensional ratios in the drawings are exaggerated, and thus are different from actual ratios in some cases.

FIG. 1 schematically illustrates one embodiment of the medical device representing an example of the inventive medical device disclosed here. This disclosed medical device is configured to grind a substance in a body lumen such as arteriosclerosis in a blood vessel. The terms "grind" and "grinding" as used here are not limited to any particular operation or manner of acting on the substance, and include operations such as grinding, scraping, abrading, ablating, macerating, grinding and otherwise breaking down desired substance or material into particles or other smaller units of material to facilitate removal from the living body (e.g., blood vessel).

The medical device 100 shown in FIG. 1 can be used to grind a stenosis 30 such as shown in FIGS. 2A, 2B from a blood vessel 10, which stenosis can be constituted by a thrombus, calcified lesion, etc. Referring initially to FIG. 1, the medical device 100 may include a treatment member 102 and an operation unit 104 configured to transmit a rotation driving force to the treatment member 102 to rotate the treatment member 102. The operation unit 104 may be housed in a handle 108.

The operation unit 104 includes a motor 128 that produces a rotational output force. The operation unit 104 also includes a drive mechanism section 122 for transmitting or applying the rotational output shaft of the motor 128 to the drive shaft 114. The drive mechanism section 122 includes a drive gear 124 and a driven gear 120 that mesh with one another so that rotation of the drive gear 124 results in rotation of the driven gear 120. The motor 128 serves as a driving source and includes a rotatable motor shaft 130 to which the drive gear 124 is fixed so that the motor shaft 130 and the drive gear 124 rotate together as a unit. Operation of the motor 128 causes rotation of the motor shaft 130, which in turn results in rotation of the drive gear 124. The proximal end of the drive shaft 114 may be fixed to the driven gear 120 so that the drive shaft 114 and the driven gear 120 rotate together as a unit. Thus, the operation of the motor 128 and the rotation of the motor shaft 130 are transmitted to the treatment member 102 by way of the drive gear 124, the driven gear 120 and the drive shaft 114. A power supply section 106 that includes a battery 126 may be provided in the handle 108 and connected to the motor 128 to supply power to the motor 128. A power cable 110 may be connected to the battery 126 to supply power. FIG. 1 also shows that the medical device 100 may be provided with an aspiration tube 112 to remove (i.e., draw-away or suck-away) debris resulting the grinding of the substance 30.

The drive shaft 114 may be comprised of a tubular drive shaft that is hollow so that a central lumen extends throughout the entire axial extent of the drive shaft 114. The drive shaft 114 may preferably be flexible, but also well suited to transmitting the rotational output of the motor unit from the proximal end of the drive shaft 114 to the distal end 117 of the drive shaft 114 at which the treatment member 102 is located. The drive shaft 114 may be any desired construction. For example, the drive shaft 114 may be constituted by a multi-layer structure. As an example, the drive shaft 114 may be configured as a multi-layered coiled tube made from, for example, a polyolefin such as polyethylene or polypropylene, polyamides, polyesters such as polyethylene terephthalate, fluorine series such as PTFE Polymer, PEEK, polyimide, or combinations thereof. The tubular drive shaft can also be provided with reinforcement. The size of the drive shaft may be appropriately selected. Examples of an appropriate size include an inner diameter of 0.40 mm to 1.40 mm and an outer diameter of 0.6 mm to 1.6 mm.

The drive shaft 114 is preferably a tubular drive shaft as mentioned above so that the drive shaft includes a lumen defining a guidewire-receiving passage. The guidewire passes through the lumen in the drive shaft and allows the drive shaft 114 together with the treatment member 102 to be navigated through the living body (e.g., the lumen of a blood vessel) to position the treatment member 102 at the desired place adjacent substance to be ground.

The drive shaft 114 may be housed in a tubular outer sheath 116. The outer sheath 116 may be a tubular body that accommodates the drive shaft 114 so that the drive shaft 114 is rotatable and axially movable relative to the outer sheath 116 and in the outer sheath 116. The material forming the outer sheath 116 is not limited to a particular material. By way of example, the outer sheath 116 may be made of polyethylene, polypropylene, polyolefin such as polyethylene terephthalate, polyester such as polyamide terephthalate, fluorine-based polymers such as PTFE, PEEK, polyimide, and the like.

The operation of the motor 128 can be controlled by way of a switch 132. Operating or turning on the switch 132 causes the motor 128 to operate and rotate the motor shaft 130. As a result, the drive gear 124 rotates and in turn rotates the driven gear 120, which meshes with the drive gear 124. The rotation of the driven gear 120 results in rotation of the drive shaft 114 and ultimately rotation of the treatment member 102.

Figure 3:
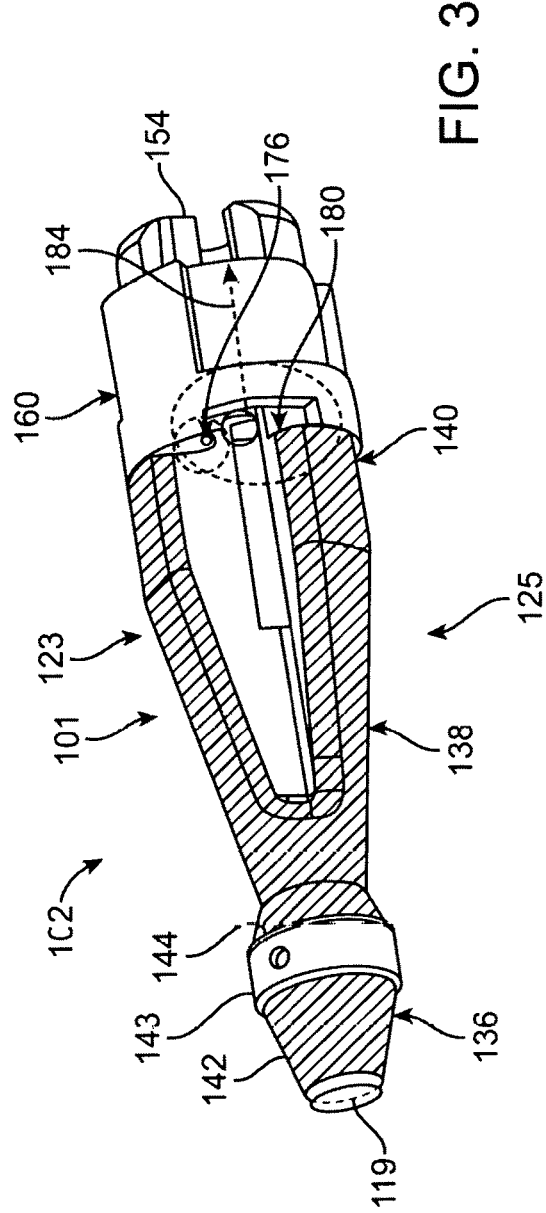
FIG. 3 is a perspective view of one version of the treatment member forming part of the medical device shown in FIG. 1.

FIGS. 2A and 2B shows a state of grinding a stenosis 30 in a blood vessel 10 using the medical device 100 according to this embodiment. As shown in FIGS. 2A and 2B, when grinding the stenosis 30 on a vessel wall 20 of the blood vessel 10. Next, when the drive shaft 114 is rotated, as shown in FIG. 3, the rolling structure 101 rotates and the third grinding part 125 and the first grinding part 123 rotate the inside of the living body lumen of the stenosis 30 can be ground. At this time, the diameter of the bottom portion 127 of the constricted portion 126 becomes the first diameter. The diameter of the annular portion 112 (see FIG. 3), and the diameter of the second annular portion 111 (see FIG. 3), it is possible to prevent the first grinding part 123 from coming into contact with the living tissue such as a normal blood vessel, and relatively high safety can be secured.

As shown in FIGS. 2A and 2B, the bending section 118 may be provided in the tubular outer sheath 116 and the drive shaft 114. This bending section 118 may be provided at an intermediate point along the length of the drive shaft 114 and the outer sheath 116. In this bending section 118, the outer sheath 116 and the drive shaft 114 are bent such as illustrated in FIGS. 2A and 2B. This allows the treatment unit 102 to be manipulated in a way that allows grinding of the stenosis 30 located in a blood vessel 20. That is, as the drive shaft 114 is rotated by operation of the motor 128, the treatment member 102 traces a movement path this circular or annular, as opposed to rotating about the central axis of the drive shaft 114. FIGS. 2A and 2B also illustrate that, during operation of the medical device while the treatment member 102 is positioned in the living body (blood vessel) and is being rotated, the distal end portion of the treatment member 102 is positioned distally beyond the distal-most end of the outer sheath 116.

Figure 4:
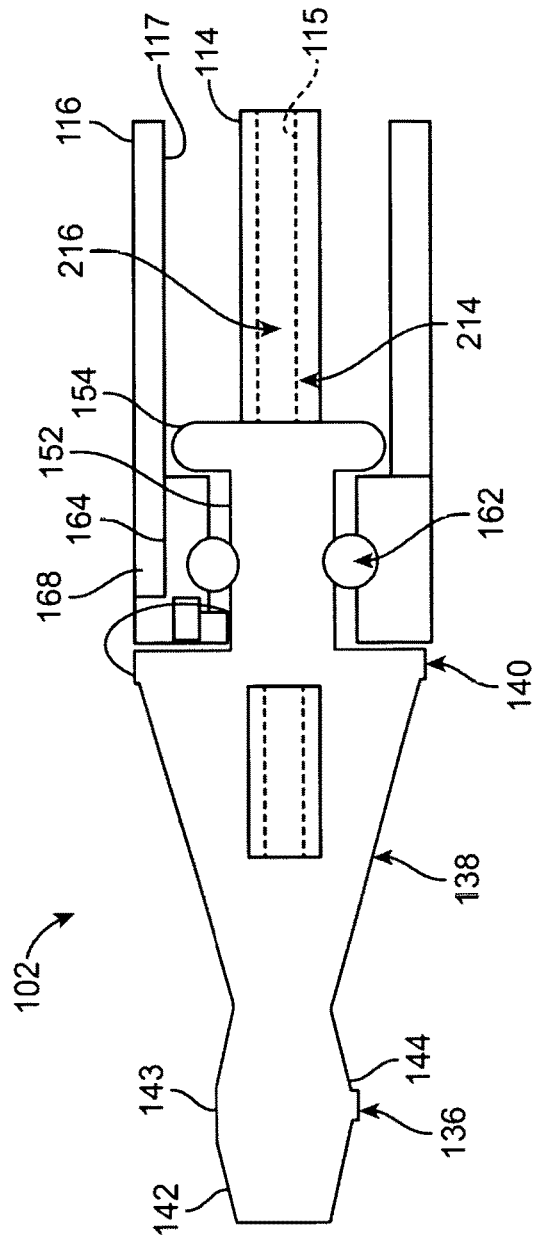
FIG. 4 is a cross-sectional view of the treatment member illustrated in FIG. 3.

FIGS. 3 and 4 illustrate additional details associated with the treatment member 102 that is connected to the distal end 214 of the drive shaft 114. FIGS. 3 and 4 illustrate the centrally located guidewire lumen 115 that may be centrally provided in the drive shaft 114 for receiving a guidewire as discussed above. As mentioned above, during operation of the medical device, the distal end portion of the treatment member 102 is positioned distally beyond the distal-most end of the outer sheath 116. FIGS. 3 and 4 show that the treatment member 102 that extends distally beyond the distal-most end of the tubular outer sheath 116 and is thus exposed (for example, the treatment member 102 not covered by the outer sheath 116). The treatment member 102 that is exposed distally beyond the distal end of the outer sheath 116 during operation may be comprised of a distal-most end portion 136, an intermediate portion 138 and a proximal end portion 140. The intermediate portion 138 is positioned axially between the distal-most end portion 136 and the proximal end portion 140. The distal-most end portion 136, the intermediate portion 138 and the proximal end portion 140 may preferably be configured to facilitate grinding of the substance in the body lumen (e.g., stenosis S in a blood vessel BV). One way of accomplishing this result is to provide the distal-most end portion 136, the intermediate portion 138 and the proximal end portion 140 of the treatment member 102 with a coating that helps facilitate the grinding of the substance in the body lumen. An example of the coating is a diamond grind coating.

The distal-most end portion 136 of the treatment member 102 is comprised of a distally tapering portion 142 and a proximally tapering portion 144. The proximally tapering portion 144 is positioned proximal of the distally tapering portion 142. The distally tapering portion 142 constantly tapers in a narrowing manner towards the distal-most end of the treatment member 102 while the proximally tapering portion 144 constantly tapers in a narrowing manner towards the proximal-most end of the treatment member 102. The distal-most end portion 136 of the treatment member 102 also comprises a constant outer diameter intermediate portion 143 positioned between the distally tapering portion 142 and the proximally tapering portion 144. In the illustrated embodiment, the coating that helps facilitate the grinding of the substance in the body lumen is not provided on the constant outer diameter intermediate portion 143. Of course, the coating applied to the outer surface of the remainder of the treatment member 102 may also be provided on the outer surface of the constant outer diameter intermediate portion 143.

The intermediate portion 138 may be a tapering portion as illustrated in FIGS. 3 and 4 in which the intermediate portion tapers in a constant manner along its entire extent from the proximal-most end of the intermediate portion 138 to the distal-most end of the intermediate portion 138. The intermediate portion 138 tapers towards the distal-most end of the treatment member 102 so that the outer diameter of the intermediate portion 138 gradually narrows in the distal direction. The proximal end portion 140 may possess a constant outer diameter along its entire axial extent as shown in FIGS. 3 and 4.

The treatment member 102 is also provided with at least one window or through opening that communicates with the hollow interior or lumen inside the treatment member 102. The treatment member 102 may include a plurality of circumferentially spaced-apart windows or through openings. As mentioned above, each of the windows or through openings opens into and communicates with the hollow interior or lumen (gateway lumen) in the treatment member 102. The lumen or hollow interior of the treatment member 102 is in communication with the lumen 117 in the outer sheath 116 as shown in FIG. 4. The aspiration tube 112 shown in FIG. 1 is connected to or fluidly communicates with the lumen 117 in the outer sheath 116. The aspiration tube 112 is connected to an aspiration source or suction device 111 schematically illustrated in FIG. 1.

During operation of the medical device 100, the treatment member 102 is rotated by operation of the motor 128 to grind the substance 30 in the body lumen 10 (e.g., stenosis in the blood vessel). While the treatment member 102 is grinding the substance in the body lumen, the suction source 111 is operated to draw debris resulting from the grinding operation through the windows or through openings 150 in the treatment member 102, into the lumen or hollow interior in the treatment member 102, and into the lumen 117 in the outer sheath 116. The debris is then drawn out of or removed from the body lumen by way of the suction device 111.

As illustrated in FIG. 4, the proximal end portion of the treatment member 102 includes a reduced outer diameter portion defining a shaft portion 152 of the treatment member 102. This reduced-outer diameter shaft portion 152 of the treatment member 102 represents a seating region for receiving an outer tubular member 160 representing a shaft bearing or bush member. A lumen extends throughout the entire axial extent of the outer tubular member 160 (i.e., passes through the outer tubular member 160), and the reduced-outer diameter shaft portion 152 of the treatment member is positioned in the lumen that extends throughout the entire axial extent of the outer tubular member 160. The tubular member 160 is rotatable relative to the treatment member 102. That is, as described above, the treatment member 102 is rotatably driven by way of the drive shaft 114, and the treatment member 102 rotates relative to the tubular member 160.

An axially extending lumen extends throughout the entire length of the reduced-outer diameter shaft portion 152 (for example, passes through the reduced-outer diameter shaft portion 152). This lumen in the reduced-outer diameter shaft portion 152 communicates with and is coaxial with the lumen 115 in the drive shaft 114. The lumen in the reduced-outer diameter shaft portion 152 is also coaxial with the open end 119 at the distal-most end of the treatment member 102 shown in FIG. 3 and opens into and communicates with the lumen in the treatment member 102.

A bearing may be positioned between the outer surface of the reduced outer diameter shaft portion 152 and the inner surface of the outer tubular member 160 to facilitate the relative rotation between the reduced outer diameter shaft portion 152 and the outer tubular member 160. The bearing may be of any desired configuration, including a plurality of roller bearings 162 as shown in FIG. 4. The roller bearings 162 help facilitate relative rotation between the treatment member 102 and the outer tubular member 160.

As illustrated in FIG. 4, the outer peripheral surface of the outer tubular member 160 may be recessed to define a radially inwardly recessed portion defining a recess 164. The recess 164 is of limited circumferential extent (i.e., the recess 164 does not extend around the entire circumferential extent of the outer tubular member 160) so that the recess 164 possesses a circumferential extent less than 360°, preferably less than 180°. The recess 164 extends from the proximal-most end of the outer tubular member 160 towards the distal end of the outer tubular member 160. The recess 164 thus opens to the proximal-most end of the outer tubular member 160 and extends less than the entire axial extend of the outer tubular member 160 so that the distal-most end of the recess 164 is defined by a wall 166. FIG. 4 illustrates that the recess 164 in the outer surface of the outer tubular member 160 receives a distally extending projection at the distal end portion of the outer sheath 116. The engagement between the distally extending projection 168 of the outer sheath 116 and the recess 166 in the outer tubular member 160 rotationally fixes the outer sheath 116 and the outer tubular member 160 so that the outer sheath 116 and the outer tubular member 160 do not rotate relative to each other. Thus, when the treatment member 102 is rotated by operation of the motor 128, the treatment member 102 rotates relative to both the outer sheath 116 and the outer tubular member 160. The outer tubular member 160 may also include at least one radially inwardly directed protrusion 170.

Figure 5:
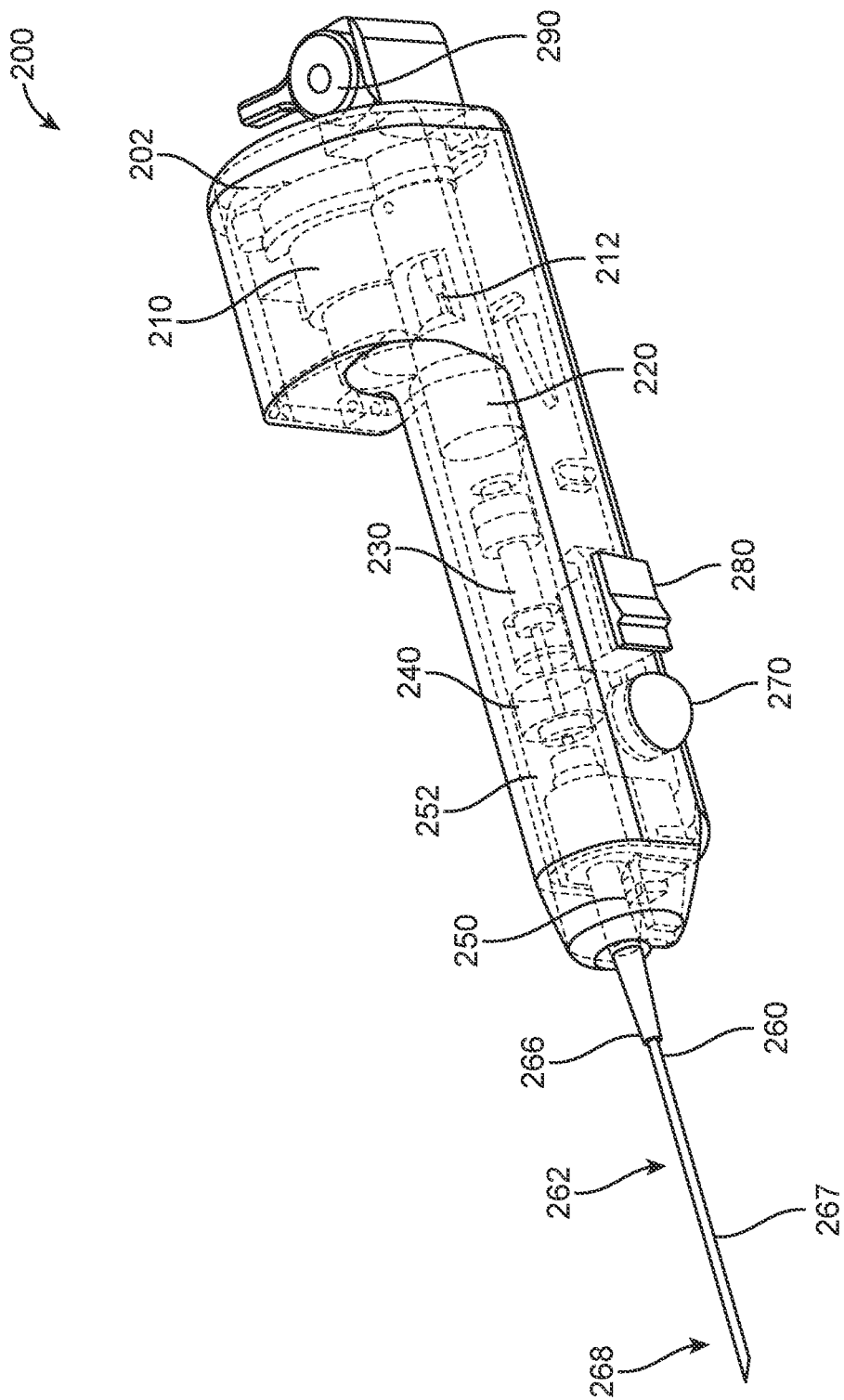
FIG. 5 is a perspective view of an exemplary handle for a medical device in accordance with an exemplary embodiment.

FIG. 5 is a perspective view of an exemplary handle 200 for a medical device 100 in accordance with an exemplary embodiment. As shown in FIG. 5, the handle 200 includes a high-speed drive source (rotational) 210, a drive shaft 212, an infusion port 220, an aspiration port 230, a seal 240, a low-speed drive source ('revolutional") 250, gearing arrangement 252, and an indicator 260 to show a bending direction of the bending section 118, and a revolution shaft 262. The revolution shaft 262 has a proximal portion 266, a distal portion 268, and a central axis of rotation 267 of the distal portion 268. In accordance with an exemplary embodiment, the handle 200 also includes a first activation switch 270 and a second activation switch 280. Although not shown, the handle 200 preferably also houses a power supply section, which can include source of power, for example, a battery, or a connection to a power source to operate the motor and other related electrical components in connection with the high-speed drive source 210 and the low-speed drive source 250. In addition, the handle 200 can include a microprocessor and/or a microcontroller, an optional memory unit, and electrical circuitry. Alternatively, the motors can be powered and controlled by a separate console.

In accordance with an exemplary embodiment, the high-speed drive source 210 is configured to provide a lower torque property than revolution, and can include a motor and a gearing arrangement comprising one or more gears. The high-speed drive source 210 is connected to the drive shaft 212, which ultimately rotates the treatment member 102 about an axis of the treatment member. The gearing arrangement allows using low speed motors to reduce manufacturing cost. Instead of using the gearing arrangement, the motor can be a motor with a hollow shaft, to which the drive shaft 212 is directly connected to rotate the treatment member 102. In accordance with an exemplary embodiment, the second activation switch 280 activates the high-speed drive source. The activation switch is activated only when the second activation switch 280 is pressed to rotate the drive shaft until pressed again, which simplifies procedure and shorten the procedure time. Alternatively, in accordance with an exemplary embodiment, the activation switch can have a first position (i.e., "OFF") and a second position (i.e., "ON"). The drive shaft 212 rotates in the "ON" position until the activation switch 280 is placed in the "OFF" position (i.e., until the rotation button is pressed again or switch to the "OFF" position.), which will prevent unintended operation by differentiating the interface of control to the first activation switch 270.

In accordance with an exemplary embodiment, the low-speed drive source 250, which provides a revolution motion (or revolving action) to the treatment member 102, and preferably has a higher torque than the high-speed drive source 210, and is configured to revolve the revolution shaft 262 within the blood vessel 10, which causes the treatment member 102 to revolve in a circular or rotate, for example, in a wiper-like motion about a central axis, which is different than an axis of rotation of the treatment member 102. The higher torque revolution provides better transmission of revolution motion to the treatment member, which makes grinding more effective and safe. For example, the central axis can be an axis formed by the outer sheath 116 proximally to the bending section 118. As set forth above, the operation of the motor (not shown) of the high-speed drive source 210 is controlled by the first activation switch 270, which causes the revolution shaft 262 to rotate in combination with the gearing arrangement 252. In accordance with an exemplary embodiment, the gearing arrangement 252 is a pair of gears. In accordance with an exemplary embodiment, the low-speed drive source 250 is only activated upon the pressing of the first activation switch 270 or application of pressure, which simplifies the procedure in combination with the second activation switch 280 and can shorten the procedure time. Upon releasing the first activation switch 270 (or releasing the pressure), the low-speed drive source 250 is no longer activated. Thus, the first activation switch 270 causes a revolution type action, for example, continuous rotation, intermittent rotation, or wiper-like action of the treatment member or flushing, aspiration, or sealing of the medical device 100. As a result, the treatment member 102 can touch more of the stenosis (or stenosed portion) 30 and make larger luminal gain of the target vessel to provide better blood flow.

In accordance with an exemplary embodiment, the rotational speeds of the treatment member 102 and the drive shaft 114, 212 are equal and can be, for example, 5,000 revolutions per minute (rpm) to 200,000 rpm. On the other hand, the rotational speed of the revolution shaft 262 can be, for example, 5 rpm to 5,000 rpm. By rotating the drive shaft at a higher speed and the revolution shaft at a slower speed (or lower speed), the luminal gain of the target vessel can be maximized with less vessel injuries. If the revolution shaft is rotated at a higher speed, as it touches to the vessel all over the outer surface of the catheter, the revolution shaft can cause trauma or spasm of the target vessel. The first activation switch 270 may only be activated while the second activation switch 280 is activated, which can help prevent unexpected injury to the vessel wall due to unintentionally touching the first activation switch 270.

In accordance with an exemplary embodiment, rather than a first activation switch 270, a manual knob (not shown) can be used to rotate the treatment member 102, for example, in a wiper-like action, which can be useful for operators who prefer manual operations. The manual knob can be connected to a locking and releasing mechanism, which can help prevent the treatment member 102 from rotating when the manual knob is not is use.

As shown in FIG. 5, the handle 200 includes a housing 202, which houses the high-speed drive source 210, the drive shaft 212, the seal 240, the low-speed drive source 250, and the gearing arrangement 252. The housing 202 is preferably made of a plastic or plastic like material, for example, from an organic polymer. In accordance with an exemplary embodiment, the housing 202 has a generally rectangular shape and can be configured to fit within a hand of a user or operator.

In accordance with an exemplary embodiment, the first activation switch 270 and the second activation switch 280 can be located on a distal portion of the housing 202. In accordance with an exemplary embodiment, the first activation switch 270 and the second activation switch 280 can be operated by thumb holding the handle 200, which provides single-hand operation. In accordance with an exemplary embodiment, the switches 270, 280 can be operated by two or more fingers, for example, the index finger on the first activation switch 270 and the middle finger on the second activation switch 280. However, depending on the operator, any of the fingers of the operator can be used to operate the first activation switch 270 and/or the second activation switch 280.

The handle 200 can also include an infusion port 220 configured to be in fluid communication with a liquid supply unit, which supplies a lubricant liquid like a saline solution (or physiological salt solution) or the like into the outer sheath 116 to reduce heat generation caused by physical frictions between static and rotating components. In addition, an aspiration port 230 is provided, which is in communication with the aspiration tube 112 to remove (for example, draw-away or suck-away) debris resulting from the grinding of the stenosis 30 (i.e., substance).

In accordance with an exemplary embodiment, the handle 200 can also include the wire fixation unit 290, which is configured to fix, for example, the guidewire 115 during grinding operations of the stenosis 30, such that that guidewire 115 does not move and is secured during the operation and/or procedure.

Figure 6:
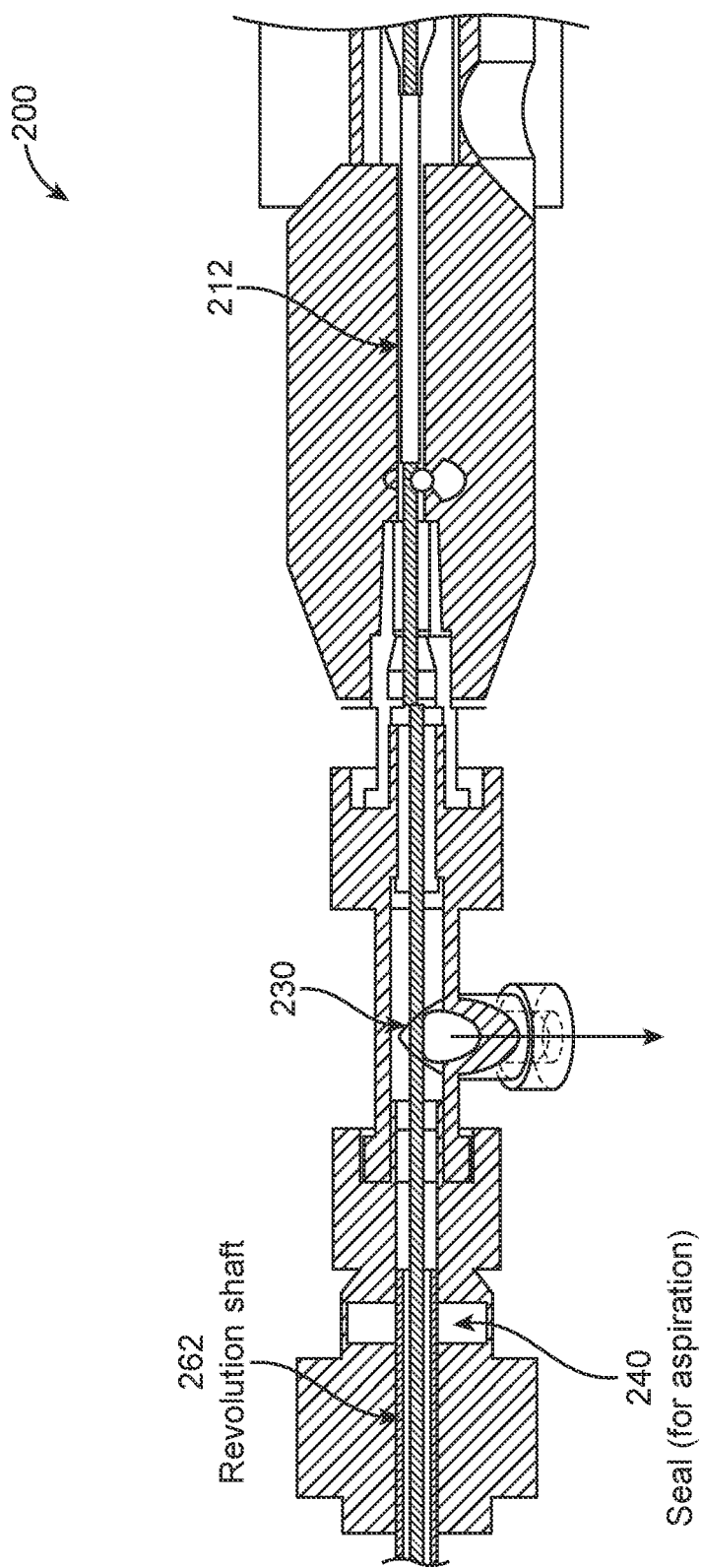
FIG. 6 is a schematic view of a handle for a medical device in accordance with an exemplary embodiment.
Figure 7:
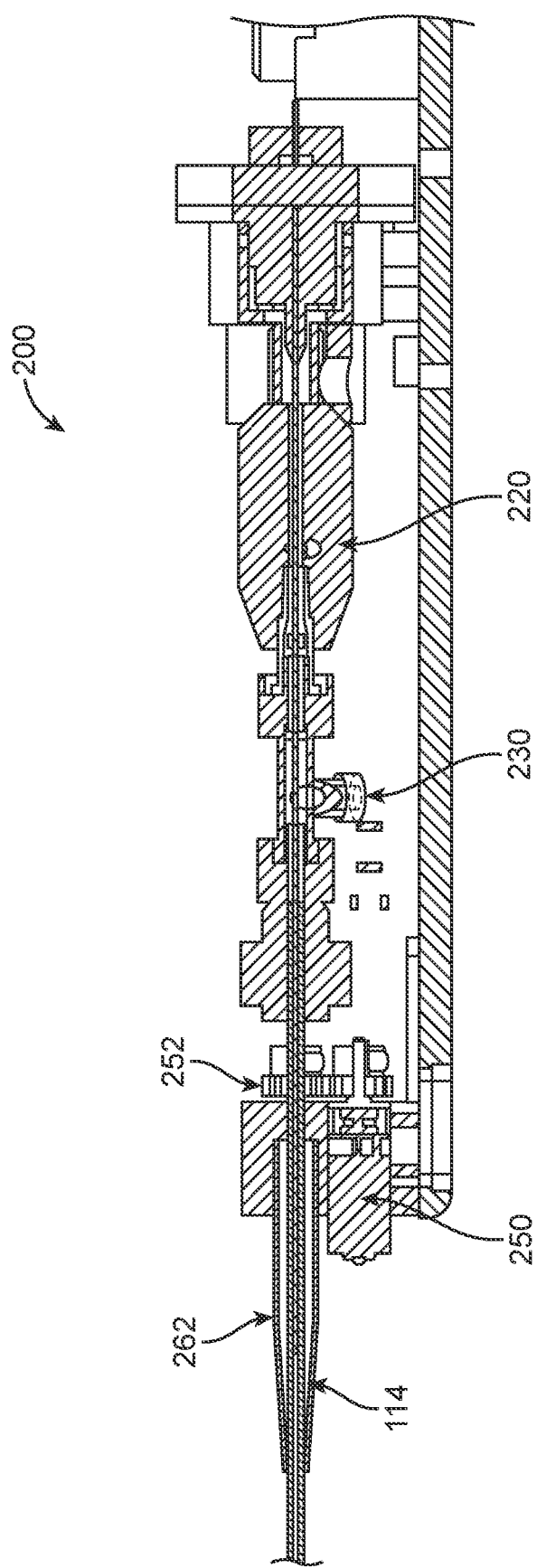
FIG. 7 is another schematic view of a handle for a medical device in accordance with an exemplary embodiment.

FIGS. 6 and 7 are schematic views of the handle 200 for a medical device as shown in FIG. 5 in accordance with an exemplary embodiment. As shown, for example, in FIG. 6, the seal 240 is preferably a bearing with a rubber seal, a PTFE O-ring, a silicone ring, or a rubber O-ring, which is configured to prevent air from entering into the aspiration port 230 so that the aspiration can create high negative pressure by liquid tight seal. The seal 240 contacts the outer surface of the revolution shaft 262 and prevents air ingress to the aspiration port 230 even when the revolution shaft 262 rotates during the first activation switch 270 is pressed. As a result, the seal 240 can continuously allow fluids or debris from the stenosis 30 to be aspirated inside the outer sheath 116, and subsequently removed from handle 200 via the aspiration port 230 even when the revolution shaft is rotating.

FIGS. 8 and 9 are views of an indicator 260 on the revolution shaft 262 indicating a direction of the bending section 118 and corresponding treatment member 102 in accordance with an exemplary embodiment. As shown in FIG. 8, on a proximal end 264 of the revolution shaft 262, an indicator 260, for example, in shape of a triangle or other shape, can be arranged to give an operator a visual indicator of the direction in which a tip 103 of the treatment member 102 and the bending section 118 of the medical device 100 are arranged or positioned within the blood vessel 10 to help the operator with the removal of the stenosis 30. For example, as shown in FIG. 8, the indicator 260 preferably corresponds to a relative position of the tip 103 of the treatment member, for example, as shown in FIG. 9.

Figure 10:
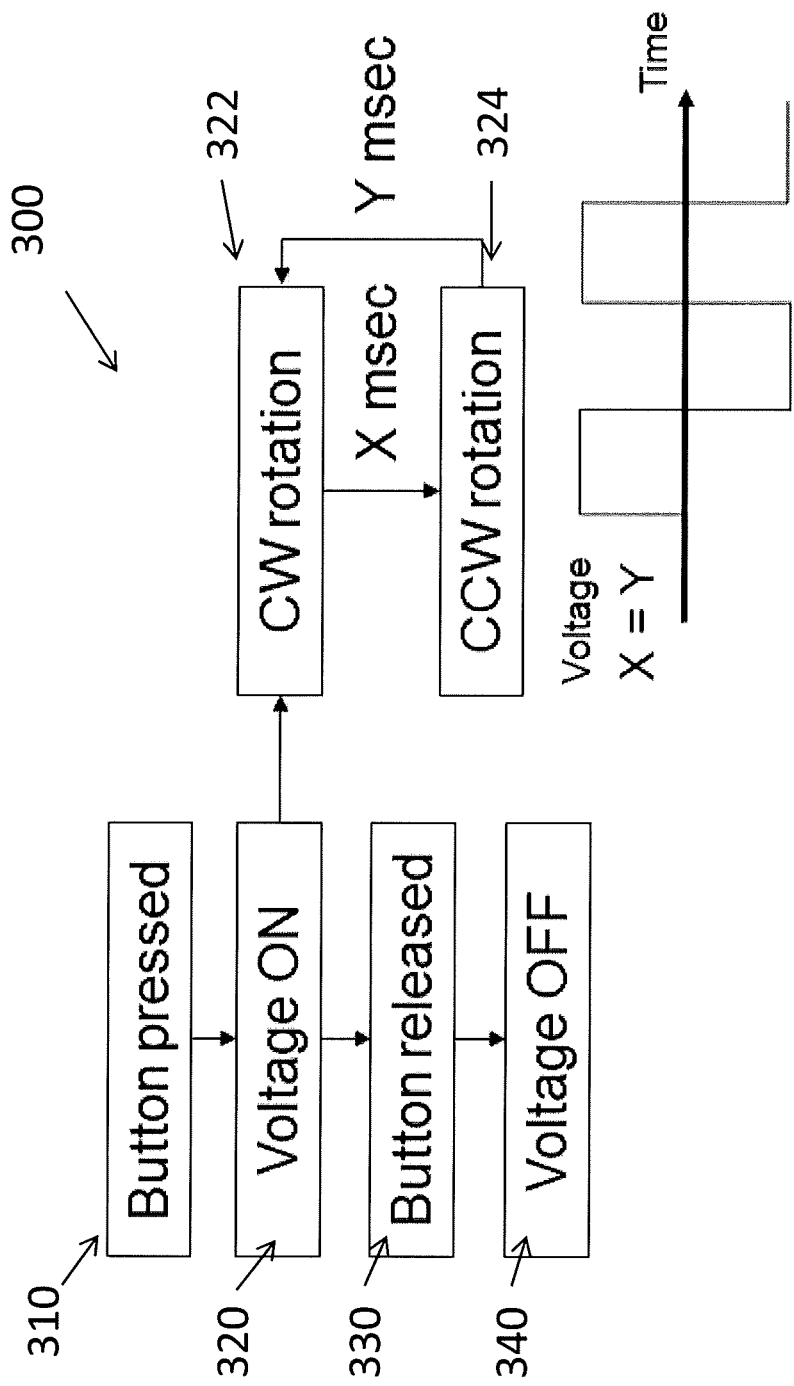
FIG. 10 is a flow chart illustrating the functions of the handle with a wiper-like action in accordance with an exemplary embodiment.

FIG. 10 is a flow chart 300 illustrating the functions of the handle 200 with a wiper-like action in accordance with an exemplary embodiment. In accordance with an exemplary embodiment, the low-speed drive source 250 can be configured to revolve the treatment member 102 in a wiper-like motion, i.e., pivoting of the treatment member 102 in a radial type motion from side to side about the central axis, which is different from the axis of the treatment member 102.

In accordance with an exemplary embodiment, in step 310, the first activation switch (or button) 270 can be pressed, which causes in step 320, the voltage within the low-speed drive source 250 to become activated. The activation of the low-speed drive source 250 causes the revolution shaft to rotate in a clockwise direction 332 for a defined period of time (for example, X milliseconds (msec)), which in turn cause the treatment member 102 and bending section 118 to revolve or pivot, for example, in a clockwise direction. After the defined period of time, the revolution shaft 262 rotates in a counterclockwise direction 324 causing the treatment member 102 and bending section 118 to rotate in the same counterclockwise direction for a predefined period of time (for example, Y msec). In accordance with an exemplary embodiment, X msec and Y msec are preferably equal to help ensure that the grinding direction of the treatment member 102 are equal, and which can help lead to a safe and an effective procedure. In accordance with an exemplary embodiment, upon releasing the first activation switch (or button) 270 in step 330, the voltage is turned off 340 to deactivate the low-speed drive source 250.

FIGS. 11A and 11B are cross-sectional views of the wiper-like action of a treatment member 102 inside a blood vessel 10 in accordance with an exemplary embodiment. As shown in FIG. 11A, the blood vessel 10 can have a non-stenosed portion, for example, a healthy vessel without calcification, and a stenosed portion (i.e., stenosis) 30.

As shown in FIG. 11B, with the wiper-like action of the treatment member 102 as disclosed herein, the treatment member 102 can be directed in wiper-like motion into the stenosed portion (i.e., stenosis) 30, for example, by rotating the handle 200. In accordance with an exemplary embodiment, an operator, for example, a physician can direct the wiper direction by rotating the handle 200 to define the grinding side, for example, by observing an angiogram. The wiper (or wiper-like) action or wiper grinding is activated by depressing or pressing the first activation switch 270 as disclosed above. In accordance with an exemplary embodiment, for example, the wiper action can be slower than rotational drive. For example, the speed of the wiper action can be, for example, 5 rpm to 500 rpm (equivalent speed when rotated in one way). In addition, the range of angles can be, for example, 5 degrees to 180 degrees, and preferably 10 degrees to 120 degrees. In accordance with an exemplary embodiment, the time of the wiper action is rather the function of (what should be determined based on) the rotation speed and rotation angle.

Figure 12:
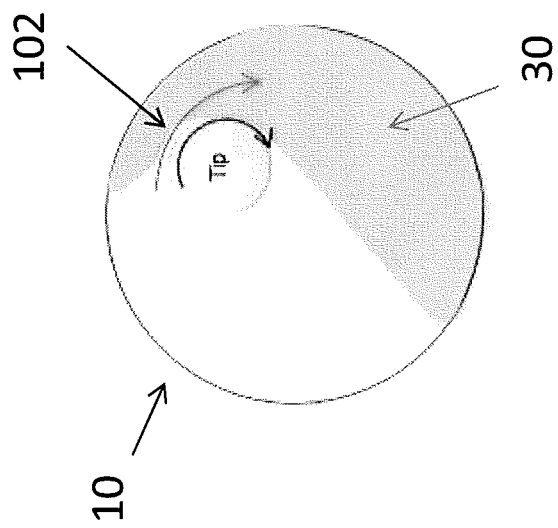
FIG. 12 is a cross-sectional view of the wiper-like action of a treatment member inside a blood vessel having an up grind action.

FIG. 12 is a cross-sectional view of the wiper-like action of a treatment member 102 inside a blood vessel 10 having an up grind action. As shown in FIG. 12, an up grind action combining rotation of the treatment member 102 in a clockwise motion and revolution of the treatment member 102 in a the clockwise direction can help provide a better surface finish and can help lessen the impact on the tip 103 of the treatment member 102. For example, in accordance with an exemplary embodiment, the up grind action can be used for smaller debris (or substances) within the blood vessel, and which can reduce embolization risks. The up grind action can also be obtained by rotating the treatment member 102 and revolution of the treatment device 102 in the same direction.

Figure 13:
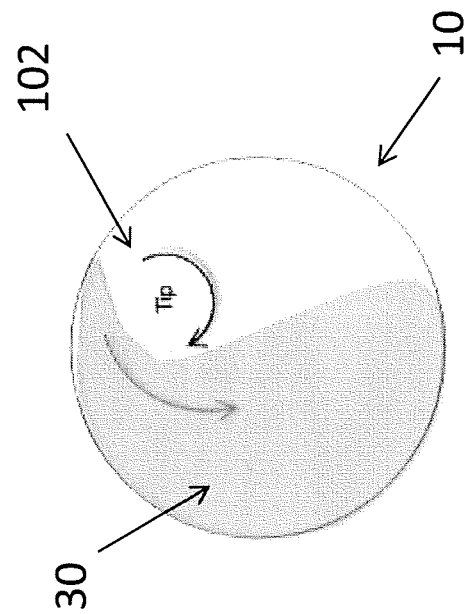
FIG. 13 is a cross-sectional view of the wiper-like action of a treatment member inside a blood vessel having a down grind action.

FIG. 13 is a cross-sectional view of the wiper-like action of a treatment member 102 inside a blood vessel 10 having a down grind action. As shown in FIG. 12, the down grind action includes rotation of the treatment member 102 in a clockwise direction and revolution of the treatment member 102 in a counterclockwise motion into the stenosed portion (i.e., stenosis) 30. For example, the down grind action can be performed with tools having for example, a diamond coating, which are durable and exhibit stable grinding performance. The down grind action can also be obtained by rotating the treatment member 102 and revolution of the treatment device 102 in opposite directions. In accordance with an exemplary embodiment, for example, both an up grind and a down grind can be used, which can provide for both durability and better surface finish for better blood flow. This effect is not limited for the wiper-like action but also can be applied to continuous or intermittent revolution actions where the revolution shaft is rotated continuously or intermittently.

Figure 14:
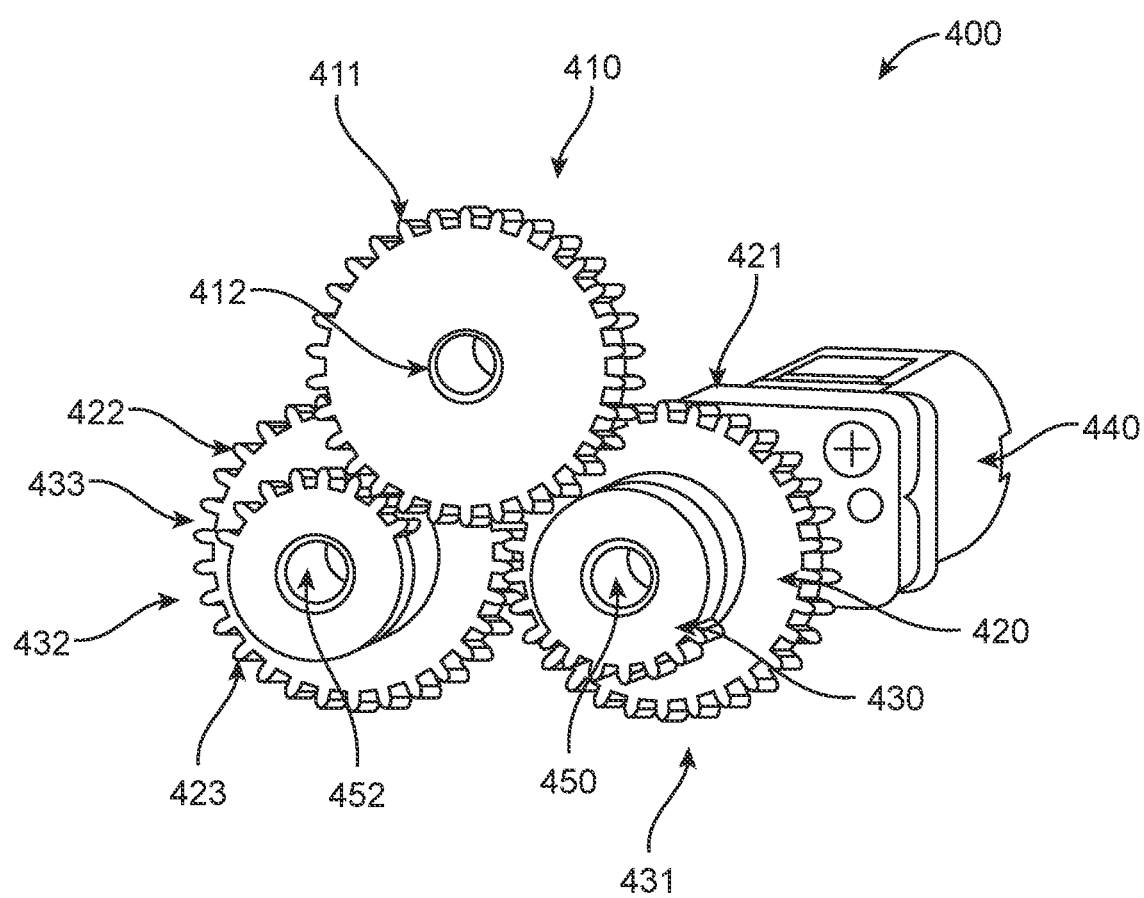
FIG. 14 is a perspective view of a gearing arrangement for a medical device having a treatment member having a wiper-like action in accordance with an exemplary embodiment.

FIG. 14 a perspective view of a gearing arrangement 400 for a medical device having a treatment member 102 having a wiper-like action in accordance with an exemplary embodiment. As shown in FIG. 14, the gearing arrangement 400 can be used in place of a microcontroller to control the clockwise and counterclockwise motion of the treatment member 102 via the revolution shaft 262 about the central axis, which is different from the rotational axis of the treatment member 102. As shown in FIG. 14, the gearing arrangement can include a motor 440, for example, a revolution motor, which rotates, for example, a first sub gear 420 having a first partial tooth gear 430. The first sub gear 420 has a plurality of teeth 421 on outer circumference, which engage a plurality of teeth 423 on an outer circumference of a second sub gear 422. The second sub gear has a second partial tooth gear 432. The first and second partial tooth gears 430, 432 are configured to engage a toothed main shaft gear 410 in an alternative arrangement, which causes a main shaft 412 of the main shaft gear 412 to rotate the revolution shaft 262 in a wiper action (or wiper-like action), that is, in a back and forth motion.

In accordance with an exemplary embodiment, the first and the second partial tooth gears 430, 432 have a series of teeth 431, 433 on approximately half the circumference or 180 degrees around the circumference of the gears 430, 432. In addition, one of the first and the second partial tooth gears 430, 432 will rotate clockwise, and the other of the first and second partial tooth gears 430, 432 will rotate in a counterclockwise direction such that a series of teeth 411 on the main shaft gear 410 will essentially be in contact with one of the first and second partial tooth gears 430, 432 continuously, and upon reach an end of the series of teeth of one of the first and the second partial tooth gears 430, 432, the engagement with the other of the first and second partial tooth gears 430, 432, will cause the main shaft gear 410 to rotate in an opposite direction. Thus, with the gearing arrangement 400 as shown in FIG. 14, the electrical control of the handle 200 can be simplified and the wiper action can be relatively free from electrical failure. In accordance with an alternative embodiment, the wiper action can be controlled by a microprocessor, which electronically changes the direction of the revolution shaft 262.

In accordance with an exemplary embodiment, the gear arrangements can be replaced any power-transmitting component like pulley, belts, and clutches.

The detailed description above describes a device handle for a medical device and treatment method. The invention is not limited, however, to the precise embodiments and variations described. Various changes, modifications and equivalents can effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A device handle for grinding substances inside a body lumen, the device handle comprising:
   a drive shaft;
   a revolution shaft;
   a high-speed drive source configured to rotate a treatment member connected to a distal end of the drive shaft; and
   a low-speed drive source connected to the revolution shaft, and wherein the revolution shaft is configured to cause the treatment member to move about a central axis of the revolution shaft, the drive shaft and the revolution shaft include a section arranged proximally and adjacent to the treatment member, which is bent, and wherein the central axis of a proximal portion of the revolution shaft is different from a central axis of the treatment member as a result of the bent section in the drive shaft and revolution shaft;
   a first activation switch for activating the low-speed drive source;
   a second activation switch for activating the high-speed drive source;
   wherein the first activation switch is only activated while the second activation switch is activated; and
   wherein the second activation switch is a button in which the drive shaft rotates once the button is pressed until pressed again.

2. The device handle of claim 1, wherein the drive shaft and the revolution shaft are coaxial in the device handle.

3. The device handle of claim 1,
   wherein the first activation switch is a button in which the revolution shaft only rotates when pressure is applied to the button.

4. The device handle of claim 1, wherein
   the high-speed drive source includes at least a motor and a gearing arrangement, the gearing arrangement configured to rotate the treatment member connected to the distal end of the drive shaft, or the high-speed drive source includes a motor with a hollow-shaft, the hollow-shaft configured to rotate the treatment member connected to the distal end of the drive shaft; and
   the low-speed drive source including at least a motor and at least one gear configured to cause the revolution shaft to move the treatment member about the central axis.

5. The device handle of claim 1,
   an infusion port configured to be in fluid communication with a liquid supply unit, which supplies a lubricant liquid into an outer sheath;
   an aspiration port in communication with an aspiration tube to remove debris resulting from the grinding of the substance inside the body lumen; and
   a power supply configured to supply power to the low-speed drive source and the high-speed drive source.

6. The device handle of claim 1, wherein the first activation switch and the second activation switch are arranged on a housing of the handle to be operated by a user's thumb.

7. The device handle of claim 1, wherein the low-speed drive source is a manually operated knob; and
the handle includes a locking and release mechanism configured to prevent the manually operated knob from rotating.

8. The device handle of claim 1, further comprising:
an indicator on a proximal side of the revolution shaft and distally of the device handle, the indicator providing an indication to an operator of a direction of the treatment member within the body lumen.

9. The device handle of claim 1, wherein the high-speed drive source has a lower torque than the low-speed drive source.

10. The device handle of claim 1, wherein rotational directions of the high-speed drive source and the low-speed drive source are in a same direction.

11. The device handle of claim 1, wherein rotational directions of the high-speed drive source and the low-speed drive source are in different directions.

12. The device handle of claim 1, further comprising:
a wire fixation unit arranged on a proximal end of the device handle and configured to secure a guidewire during the grinding of the substances inside the body lumen.

13. A device handle for grinding substances inside a body lumen, the device handle comprising:
a drive shaft;
a revolution shaft;
a high-speed drive source configured to rotate a treatment member connected to a distal end of a drive shaft;
a low-speed drive source connected to a revolution shaft;
a first activation switch for activating the low-speed drive source, the first activation switch being a button in which the revolution shaft only rotates when pressure is applied to the button;
a second activation switch for activating the high-speed drive source, the second activation switch being a button in which the drive shaft rotates once the button is pressed until pressed again;
the first activation switch configured to be activated only while the second activation switch is activated; and
wherein the revolution shaft is configured to cause the treatment member to move about a central axis of the revolution shaft, the drive shaft and the revolution shaft include a section arranged proximally and adjacent to the treatment member, which is bent, and wherein the central axis of a proximal portion of the revolution shaft is different from a central axis of the treatment member as a result of the bent section in the drive shaft and revolution shaft.

14. A method for grinding substances inside a living body using the device handle of claim 1, the method comprising:
introducing the treatment member connected to a distal end of the drive shaft into the living body and positioning the treatment member adjacent substance in the living body to be ground;
rotating the treatment member in at least a clockwise direction or a counterclockwise direction about an axis of rotation of the treatment member while the treatment member is positioned adjacent the substance to be ground in the living body to grind the substance;
rotating the revolution shaft in at least a clockwise direction or a counterclockwise direction about an axis of rotation of the revolution shaft, wherein the revolution shaft is configured to cause the treatment member to move about the central axis of the revolution shaft; and
shearing debris resulting from the grinding of the substance to reduce a size of the debris.

15. The method of claim 14, comprising:
rotating the treatment member connected to a distal end of the drive shaft with the high-speed drive source; and
rotating the revolution shaft along an outer surface of the treatment member with the low-speed drive source.

16. The method of claim 15, comprising:
activating the low-speed drive source with the first activation switch, the first activation switch being a button in which the revolution shaft only rotates when pressure is applied to the button; and
activating the high-speed drive source with the second activation switch, the second activation switch being the button in which the drive shaft rotates once the button is pressed until pressed again.

17. The method of claim 16, comprising:
arranging the first activation switch and the second activation switch on a housing of the handle to be operated by a user's index thumb.

18. The method of claim 14, wherein a tubular member that possesses a lumen is mounted on the treatment member and surrounds a portion of the treatment member, the treatment member being rotatable relative to the tubular member, the treatment member comprising a shearing portion, and the tubular member including a protrusion that projects toward the lumen of the tubular member, the method further comprising:
shearing of the debris including shearing the debris between the protrusion of the tubular member and the shearing portion of the treatment member; and
removing the debris which has been subjected to the shearing from the living body.

* * * * *